(12) United States Patent
Dai et al.

(10) Patent No.: US 6,548,537 B1
(45) Date of Patent: *Apr. 15, 2003

(54) TRIPTOLIDE PRODRUGS HAVING HIGH AQUEOUS SOLUBILITY

(75) Inventors: Dongcheng Dai, Mountain View, CA (US); Hongwei Yuan, San Mateo, CA (US); John H. Musser, San Carlos, CA (US)

(73) Assignee: Pharmagenesis, Inc., Palo Alto, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 09/798,319

(22) Filed: Mar. 2, 2001

Related U.S. Application Data

(63) Continuation-in-part of application No. PCT/US99/20150, filed on Sep. 2, 1999.
(60) Provisional application No. 60/098,809, filed on Sep. 2, 1998.

(51) Int. Cl.$^7$ ........................ A61K 3/343; C07D 307/77
(52) U.S. Cl. ........................................ 514/468; 549/456
(58) Field of Search ........................... 514/468; 549/456

(56) References Cited

U.S. PATENT DOCUMENTS

| 4,005,108 A | 1/1977 | Kupchan et al. |
| 5,962,516 A | 10/1999 | Qi et al. |
| 5,972,998 A | 10/1999 | Jung et al. |
| 6,150,539 A | 11/2000 | Musser |

FOREIGN PATENT DOCUMENTS

| WO | WO97/31921 | 9/1997 |

*Primary Examiner*—Taofiq Solola
(74) *Attorney, Agent, or Firm*—LeeAnn Gorthey; Perkins Coie LLP (57) ABSTRACT

Compounds useful in immunosuppressive, anti-inflammatory and anticancer treatment are described. The compounds are triptolide analogs with improved water solubility and generally lower toxicity than the parent compound.

13 Claims, 7 Drawing Sheets

TRIPTOLIDE PRODRUGS HAVING HIGH AQUEOUS SOLUBILITY

This application is a continuation-in-part of PCT Application No. PCT/US99/20150, filed Sep. 2, 1999 designating the U.S., which claims priority to U.S. Provisional Application Serial No. 60/098,809, filed Sep. 2, 1998, which is hereby incorporated by reference in its entirety.

FIELD OF THE INVENTION

The present invention relates to compounds useful as immunosuppressive, anti-inflammatory and anticancer agents. The compounds have good aqueous solubility and convert to biologically active compounds in vivo.

REFERENCES

Boyd, G. V. and Heatherington, K., *J. Chem. Soc. Perkin I* 2523–2531 (1973).
Ferrier, R. J., in *Carbohydrate Chemistry*, Kennedy, J. F., Ed., Clarendon Press, Oxford (1990).
Garver, L. C. et al., *J. Am. Chem. Soc.* 104:867 (1982).
Gleichmann, E. et al., *Immunol. Today* 5:324 (1984).
Hormi, O. E. O. and Nasman, J. H., *Syn. Commun.* 16:69 (1986).
Kocienski, P. J., *Protecting Groups*, Georg Thieme Verlag, Stuttgart (1994).
Korngold, R. and Sprent, J., *J. Exp. Med.* 148:1687 (1978).
Kupchan, S. M. et al., *J. Am. Chem. Soc.* 94:7194 (1972).
Kupchan, S. M. et al., U.S. Pat. No. 3,005,108 (1977).
Lipsky, P. E. et al., U.S. Pat. No. 5,294,443 (1994).
Ma, P-C. et al., *J. Chin. Pharm. Sci.* 1:12 (1992).
Mori, S. et al., *Tetrahedron* 47(27):5051–5070 (1991).
Morris, R. E., *Transplant Proc.* 23(6):2722–2724 (1991).
Morris, R. E. et al., *Transplant Proc.* 23(1):238–240 (1991).
Murase, N. et al., *Transplantation* 55:701 (1993).
Ono and Lindsey, *J. Thor. Cardiovasc. Surg.* 57(2):225–29 (1969).
Pu, L. et al., *Zhongguo Yaoli Xuebao* 11:76 (1990).
Wang, J. and Morris, R. E., *Transplantation Proc.* 23:699 (1991).
Yu et al., *Acta Pharmaceutica Sinica* 27(11):830–836 (1992).
Zheng, J. et al., *Zhongguo Yixue Kexueyuan Xuebao* 13:391 (1991).
Zheng, J. et al., *Zhongguo Yixue Kexueyuan Xuebao* 16:24 (1994).

BACKGROUND OF THE INVENTION

Immunosuppressive agents are widely used in the treatment of autoimmune disease and in treating or preventing transplantation rejection, including the treatment of graft-versus-host disease (GVHD), a condition in which transplanted marrow cells attack the recipient's cells. Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD), a condition in which transplanted marrow cells attack the recipient's cells. See, for example, coowned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), and references cited therein. Such compounds have also been reported to show anticancer activity. See, for example, Kupchan et al., 1972, 1977, as well as copending and coowned U.S. application Ser. No. 09/766,156.

The administration and therapeutic effectiveness of these compounds have been limited, however, by their low water solubility. This problem has been addressed by formulating the compounds in mixtures of ethanol and polyethoxylated castor oil (e.g., "CREMOPHOR EL™"), allowing subsequent dilution in saline for intravenous administration. However, such formulations have suffered from high toxicity, due to the high concentration of solubilizing agent required to dissolve these compounds. For example, the ratio of solubilizing agent (ethanol plus "CREMOPHOR EL™") to triptolide in such formulations is typically on the order of 1000:1 or greater, due to the poor solubility of triptolide (Morris, 1991; Morris et al., 1991). Standardization of dosage amounts is also more problematic with a suspension than with a solution.

It is therefore desirable to provide immunosuppressive compounds having comparatively low toxicity and improved water solubility. Ideally, such compounds would show immunosuppressive activity in their water soluble form, or would be convertible to an immunosuppressive form in vivo.

SUMMARY OF THE INVENTION

In one aspect, the invention provides compounds which are useful as prodrugs for immunosuppressive, anti-inflammatory and anticancer therapy. The compounds are derivatives of triptolide having hydrophilic substituents, represented by structures I–III, as shown and described below. The compounds possess greater water solubility than the non-derivatized parent compound, triptolide, and, in most cases, are effective to hydrolytically convert to the parent compound in vivo.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

"Alkyl" refers to a fully saturated acyclic monovalent radical containing carbon and hydrogen, and which may be branched or a straight chain. Examples of alkyl groups are methyl, ethyl, n-butyl, t-butyl, n-heptyl, and isopropyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably mono-unsaturated, radical containing carbon and hydrogen, and which may be cyclic, branched or a straight chain. "Lower alkenyl" refers to such a radical having one to four carbon atoms.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl)ammonium, phenylethylbenzylammonium, dibenzylethylenediammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

A "triptolide derivative" or "triptolide analog," as described herein, refers to a compound based on triptolide, 16-hydroxytriptolide or tripdiolide (2-hydroxytriptolide) which is derivatized at the 12,13-epoxy group or at the lactone ring of the parent compound.

For the purposes of the current disclosure, the following numbering scheme is used for triptolide and triptolide analogs:

II. Triptolide Analogs

This section describes the preparation of compounds as represented by structures I–III described below. The present compounds, which are derivatives of triptolide having hydrophilic substituents, possess greater water solubility than the non-derivatized starting compound, and are effective to hydrolyze and convert in vivo to the parent compound. The compounds are useful as prodrugs for immunosuppressive and anti-inflammatory applications. Although each of structures I–III shows a compound modified at one location on the triptolide nucleus, compounds having more than one such modification are also contemplated.

The compounds of the invention may be prepared from triptolide, as obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for preparing triptolide and some of its derivatives (e.g. tripdiolide and 16-hydroxytriptolide) are known in the art and are described, for example, in Kupchan et al. (1972, 1977); Lipsky et al. (1994); Pu et al. (1990); and Ma et al. (1992).

A. Compounds of Structure I

In the compounds of structure Ia–b, $R^3$ is H or —(C=O)R, where R is lower alkyl, and $OR^1$ is a hydrolyzable, hydrophilic group, e.g. a carboxylic ester, an inorganic ester, or a mono-, di- or trisaccharide linked to the parent compound via an anomeric oxygen. The carboxylic or inorganic ester has a central atom selected from carbon, sulfur, phosphorus, and boron, and attached to the central atom, at least one oxygen atom, and at least one group of the form —O—Y—Z or —Y—Z. In this group, Y represents a branched or unbranched $C_1$–$C_6$ alkyl or alkenyl chain, and Z represents hydrogen, or, preferably, a polar group selected from keto, aldehyde, carboxylate, carboxylic ester, hydroxy, alkoxy, polyether, thiol, alkylthio, amino, ammonium, alkylamino, alkylammonium, cyano, nitro, sulfate, nitrate, phosphate, or a 5- to 7-membered heterocyclic ring whose ring atoms are selected from the group consisting of carbon, nitrogen, oxygen and sulfur. where the ring atoms include 3 to 6 carbon atoms and, typically, no more than two heteroatoms. Non-aromatic heterocycles are preferred. Such heterocycles include, for example, pyrrolidine, piperazine, and morpholine. Z may also represent multiple polar groups attached to the alkyl or alkenyl chain, as in an amino acid moiety (see e.g. groups (f)–(g) below).

Examples of such inorganic esters include sulfites (—O—S(=O)—OR), sulfinates (—O—S(=O)—R), sulfates (—O—S(=O)$_2$—OR), sulfonates (—O—S(=O)$_2$—R), phosphates (—O—P(=O)(OR)$_2$), phosphonates (—O—P(=O)R(OR)), and borates (—O—B(OR)$_2$), where R is hydrogen or, more typically, lower alkyl.

Where Z includes an anionic species such as a carboxylate, the positively charged counterion is preferably an inorganic metal, such as Na$^+$, K$^+$, or Mg$^{+2}$, or a protonated organic amine, e.g. tromethamine (tris(hydroxymethyl)aminomethane). Where Z includes a basic amine, the compound may take the form of a protonated salt, with a negatively charged counterion such as chloride, bromide, iodide, acetate, oxalate, maleate, fumarate, mesylate or tosylate. Also includes are zwitterionic structures such as (f) and (g) below.

Preferably, R$^1$ is selected from (a)–(g) below:

where each R' is independently lower alkyl, R" is H or lower alkyl, m=1–2, n=1–4, and X=CH$_2$, O, or NR".

The hydrophilic nature of the substituents increases the aqueous solubility of the compounds, and hydrolysis of OR$^1$ (e.g in vivo) regenerates the unsaturated lactone (butenolide) of triptolide.

The compounds of structure Ia and Ib may be prepared by reaction of the unsaturated lactone (butenolide) with base, e.g. sodium hydride in dry THF, to generate an enolate, followed by alkylation with an electrophilic reagent such as R$^1$—X, where X is a displacable leaving group, or an activated acyl reagent, such as an acid chloride, anhydride, or carbonyl imidazole (see Hormi et al. and Garver et al.). To prepare compounds in which R$^1$ is (f) or (g) above, an amine-subsituted cyclic anhydride may be used. For example, where n=1, one such compound would be 2-dimethylamino succinic anhydride.

Figure 1A:
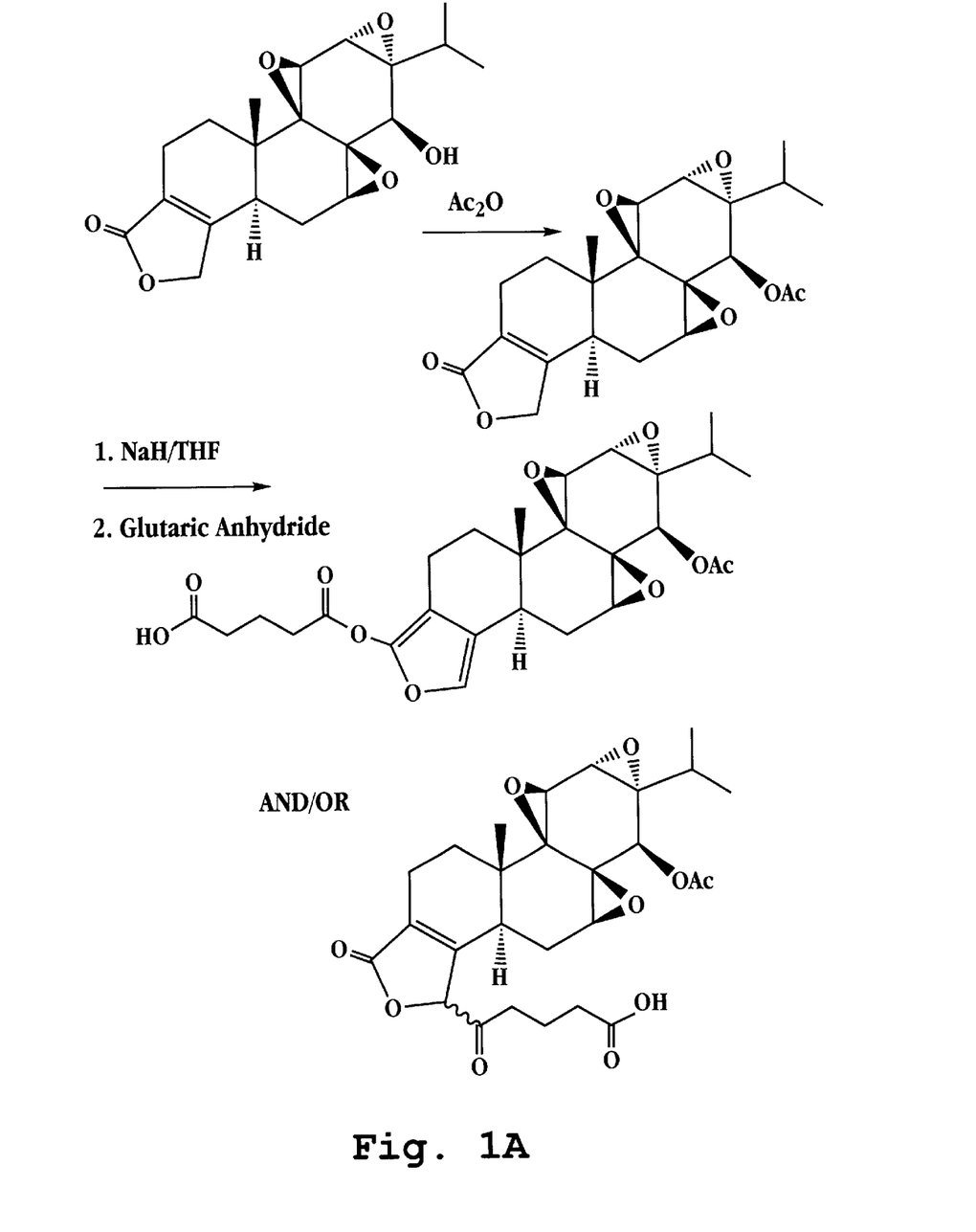
FIG. 1A shows the preparation of triptolide derivatized at the lactone ring, in accordance with structures Ia and Ic.

See, for example, FIG. 1A, wherte butenolide enolate prepared by extraction of the acidic hydrogen at C19 is acylated with glutaric anhydride, to give the carboxylic acid-terminated ester derivative. This product is energetically favored by formation of the aromatic furan nucleus. However, an alternate structure, shown above as structure Ib, may also be formed, by extraction of the acidic hydrogen at C5. The reaction products may be separated by conventional methods, e.g. column chromatography on silica gel. Structure Ib includes a tetrasubstituted double bond (C4–C5), which is also energetically favorable, and may also be hydrolyzed to regenerate the starting triptolide structure. (In this case, some degree of racemization will occur at C5.)

Figure 2A:
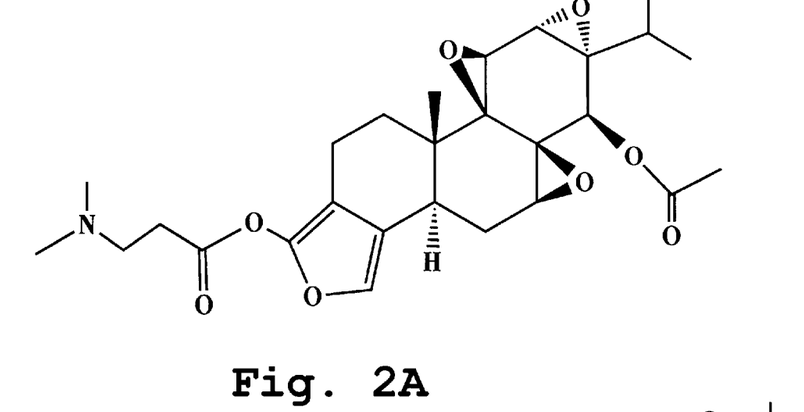
FIGS. 2A–2C show examples of specific embodiments of structure Ia.
Figure 2B:
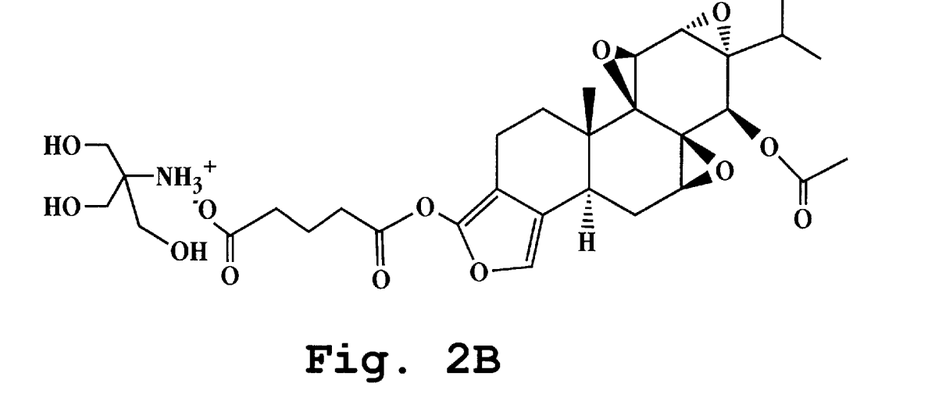
Figure 2C:
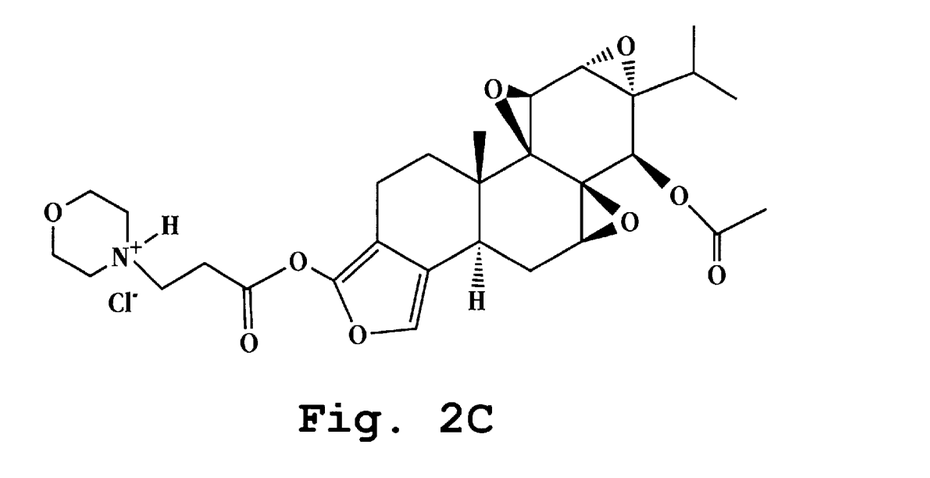

Reacting the terminal acid of the structure Ia embodiment shown in FIG. 1A with tromethamine gives the salt shown in FIG. 2B. Other representative analogs of structure Ia are shown in FIGS. 2A and 2C.

Inorganic ester derivatives are prepared by similar base-catalyzed reaction of the butenolide with the appropriate activated inorganic acid derivative, such as a halide or an anhydride (e.g. SO$_3$). For preparation of glycosides, R$^1$X is a glycosyl halide or other activated glycosyl derivative. One such type of derivative is an acetimidate activated glycoside, which may be prepared by reaction of a suitably protected glycosyl halide with a secondary amide in the presence of Ag$_2$O and base (see e.g. Ferrier, in Kennedy, p. 352).

Note that, in the reaction shown in FIG. 1A, acylation may also occur at C19 to give a keto product, as shown. Although this product is not expected to regenerate the parent compound upon hydrolysis, it may also be therapeutically active. More generally, such products will have the structure Ic, shown below:

where R$^3$ is as defined above, and R$^2$ is of the form —(C=O)—Y—Z, where Y represents a branched or unbranched C$_1$–C$_6$ alkyl or alkenyl chain, and Z represents hydrogen, or, preferably, a polar group selected from keto, aldehyde, carboxylate, carboxylic ester, hydroxy, alkoxy, polyether, thiol, alkylthio, amino, ammonium, alkylamino, alkylamnmonium, cyano, nitro, sulfate, nitrate, phosphate, or a 5- to 7-membered heterocyclic ring whose ring atoms are selected from the group consisting of carbon, nitrogen, oxygen and sulfur, where the ring atoms include 3 to 6 carbon atoms and, typically, no more than two heteroatoms. Non-aromatic heterocycles are preferred. Such heterocycles include, for example, pyrrolidine, piperazine, and morpholine. Z may also represent multiple polar groups attached to the alkyl or alkenyl chain, as in an amino acid (see e.g. groups (f)–(g) below).

Where Z includes an anionic species such as a carboxylate, the positively charged counterion is preferably an inorganic metal, such as $Na^+$, $K^+$, or $Mg^{+2}$, or a protonated organic amine, e.g. tromethamine (tris (hydroxymethyl)aminomethane). Where Z includes a basic amine, the compound may take the form of a protonated salt, with a negatively charged counterion such as chloride, bromide, iodide, acetate, oxalate, maleate, fumarate, mesylate or tosylate. Also includes are zwitterionic structures such as (f) and (g) below.

In structure Ic, $R^2$ is preferably selected from (a)–(g) below:

where each R' is independently lower alkyl, R" is H or lower alkyl, m=1–2, n=1–4, and X=$CH_2$, O, or NR".

In preparing these compounds, as well as those in accordance with structures II and III, below, it is generally desirable to protect the hydroxyl group at the C14 position. Therefore, $OR^3$ in these structures is preferably —O(C=O)R, where R is lower alkyl. For ease of preparation, a simple ester such as acetyl is typically employed.

Also provided are aminofuranoid triptolide derivatives, as represented by structure Id below, where $R^3$ is as defined above, and each $R^4$ is independently lower alkyl or together they form a 5- to 7-membered heterocyclic ring whose ring atoms are selected from the group consisting of carbon, nitrogen, oxygen and sulfur, where the ring atoms include 3 to 6 carbon atoms and, typically, no more than two heteroatoms. Non-aromatic heterocycles are preferred. Such heterocycles include, for example, pyrrolidine, piperazine, and morpholine. The compound may also be provided as a protonated amine salt.

Figure 1B:
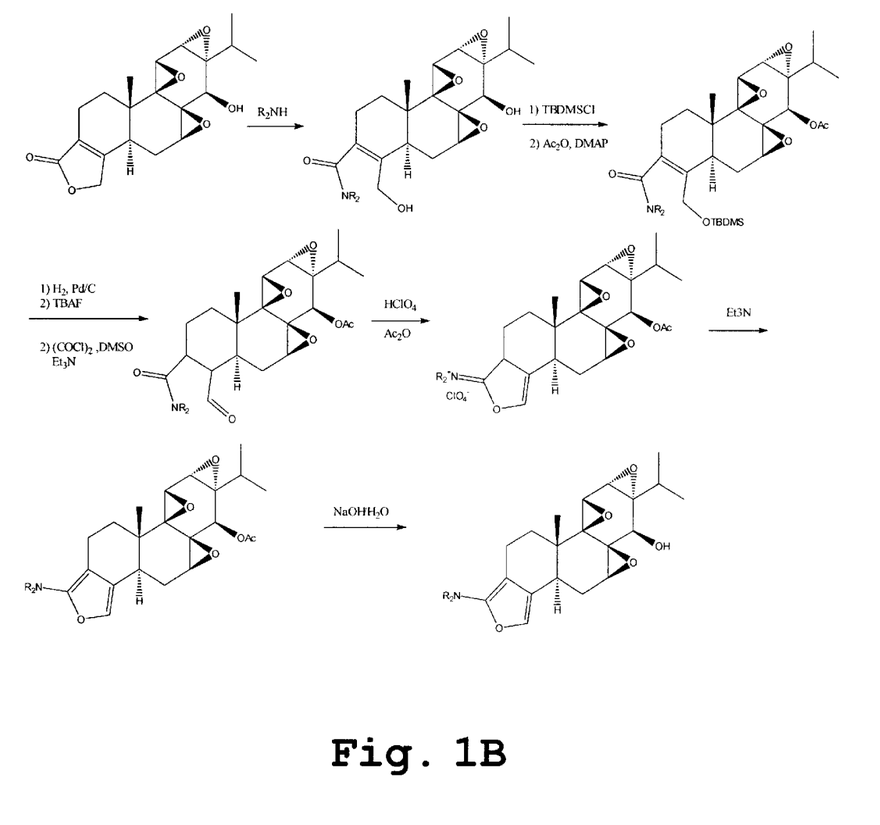
FIG. 1B shows the preparation of an aminofuran triptolide derivative, in accordance with structure Id.

Compounds of structure Id can be prepared as illustrated in FIG. 1B and described in Example 2 (see also Boyd et al., 1973). The triptolide lactone ring is cleaved with a secondary amine, such as morpholine, and the resulting primary alcohol is protected, e.g. as the t-butyldimethylsilyl ether. The secondary alcohol at C14 is acylated. The C3–C4 double bond is then hydrogenated, followed by deprotection and oxidation of the primary alcohol to the aldehyde. Treatment with acetic anhydride followed by perchloric acid gives the cyclized product as shown in FIG. 1B. Treatment with base, e.g. triethylamine, gives the enamine.

Under suitable hydrolytic conditions, e.g. in vivo, the enamine is hydrolyzed to regenerate the original lactone structure.

B. Compounds of Structure II

In another embodiment, the triptolide analogs are of the structure II, as shown above. The group $OR^3$ is as defined above, and is preferably lower acyl, e.g. acetyl. The group $OR^5$ is preferably of the form —O—Y—Z or —O—(C=O)—Y—Z, where Y is a branched or unbranched $C_1$–$C_6$ alkyl or alkenyl chain, and Z is hydrogen or a polar group selected from keto, aldehyde, carboxylate, carboxylic ester, amino, alkylamino, hydroxy, alkoxy, polyether, thiol, alkylthio, cyano, nitro, inorganic ester, or a 5- to 7-member heterocyclic ring whose ring atoms are selected from the group consisting of carbon, nitrogen, oxygen and sulfur, where the ring atoms include 3 to 6 carbon atoms, and, typically, no more than two heteroatoms. $R^5$ may also be a mono-, di- or trisaccharide linked to C14 at an anomeric center.

Again, where Z includes an anionic species such as a carboxylate, the positively charged counterion is preferably an inorganic metal, such as $Na^+$, $K^+$, or $Mg^{+2}$, or a protonated organic amine, e.g. tromethamine. Where Z includes a basic amine, the compound may take the form of a protonated salt, with a negatively charged counterion such as chloride, bromide, iodide, acetate, oxalate, maleate, fumarate, mesylate or tosylate. Also includes are zwitterionic structures such as (f) and (g) below.

Preferably, $R^5$ is selected from (a)–(g) below:

(a)
(b)
(c)
(d)
(e)
(f)
(g)

where R' is lower alkyl, R" is H or lower alkyl, m=1–2, n=1–4, and X=CH$_2$, O, or NR".

Figure 3:
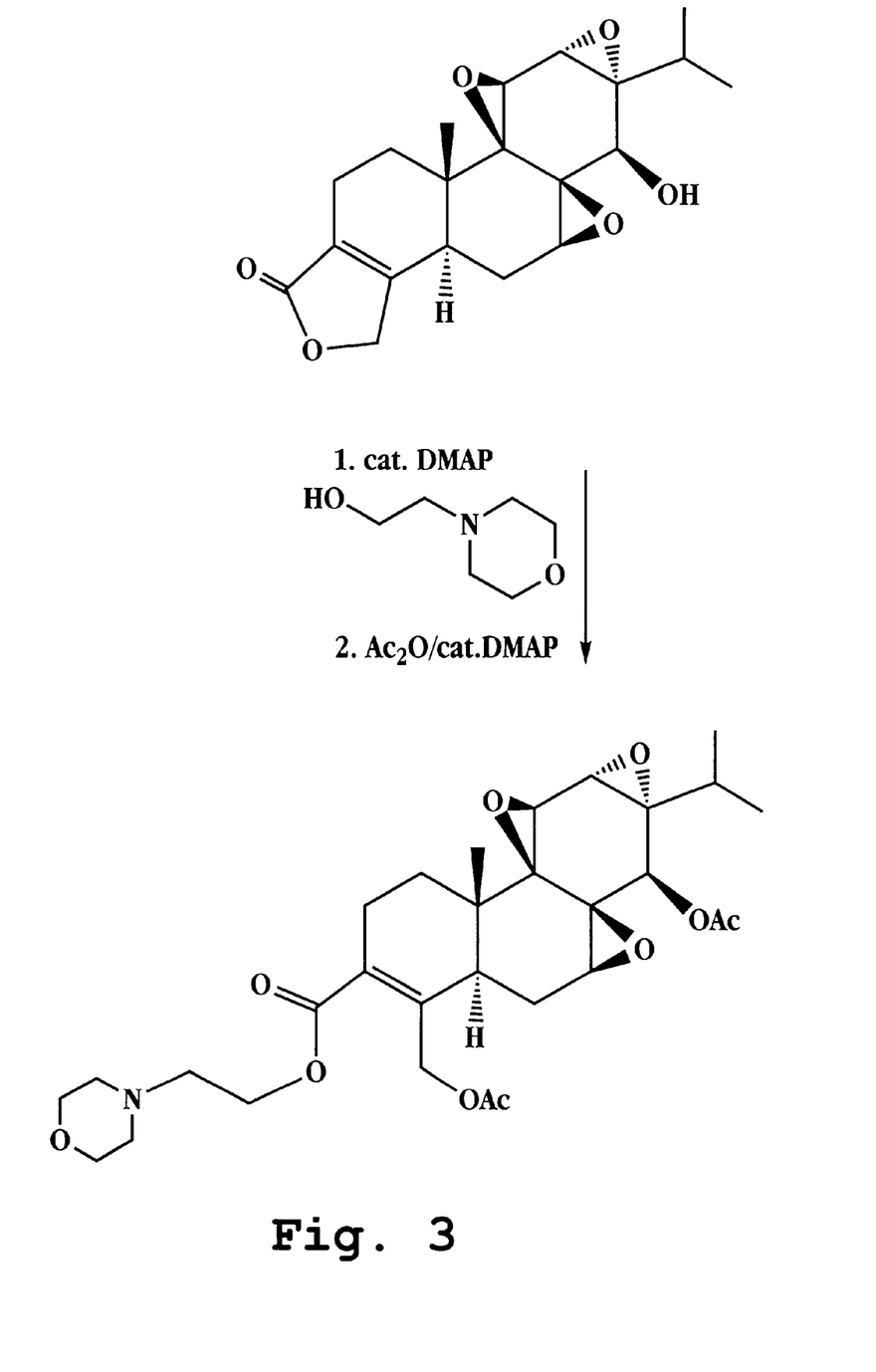
FIG. 3 shows the preparation of a lactone ring-opened derivative of triptolide, in accordance with structure II.

These compounds are prepared by transesterification of the lactone ring of triptolide with a hydroxyl-containing compound. A hydrophilic alcohol (e.g., a saccharide, or a substituted heterocycle as shown in FIG. 3) is preferably used for the transesterification, to increase the water solubility of the resulting compound. The hydroxyl generated on ring opening of the lactone is reacted with, for example, an acid chloride, as shown, to give a hydrolyzable group, such as an ester, from which the alcohol may be regenerated hydrolytically in vivo.

Figure 4A:
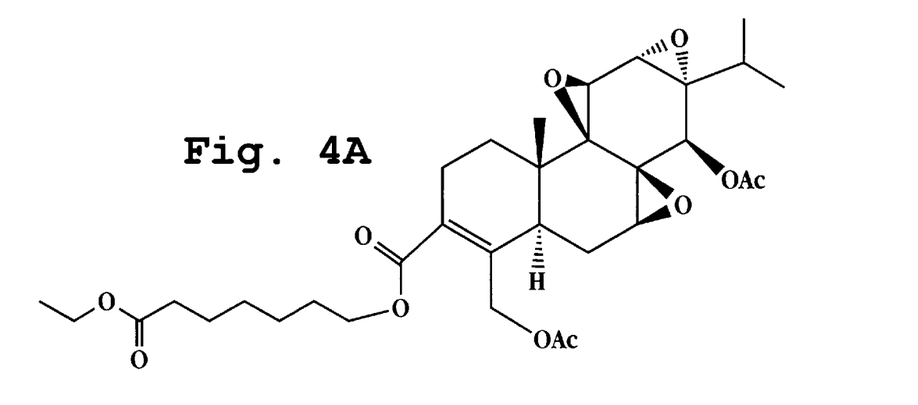
FIGS. 4A–4C show examples of specific embodiments of structure II.
Figure 4B:
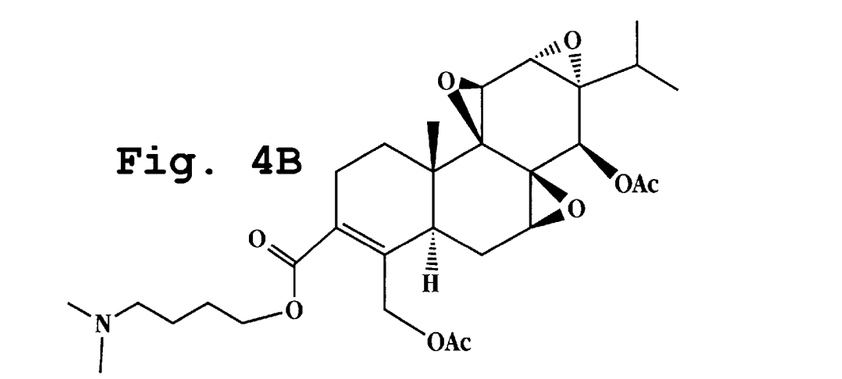
Figure 4C:
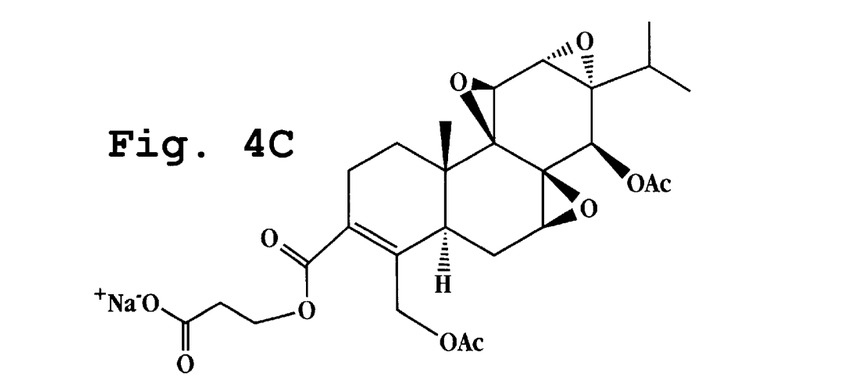

A typical synthesis is shown in FIG. 3, in which triptolide is reacted with 1-(2-hydroxyethyl)morpholine in the presence of a catalytic amount of DMAP. The free hydroxyl group which is generated, as well as the free 14-hydroxyl, are then acylated to give the final compound. Further examples are shown in FIGS. 4A–4C. When such a compound is administered as a prodrug, the ester groups are hydrolytically cleaved in vivo, and the ester and alcohol at the 3 and 4 positions react to regenerate the lactone ring of triptolide.

C. Compounds of Structure III

III

In a further embodiment, the triptolide analogs have the structure III, as shown above, where $R^6$ is a leaving group selected from the group consisting of alkyl sulfonate, fluoroalkyl sulfonate, aryl sulfonate, fluorosulfonate, trifluoroacetate, trichloroacetate, trichloroacetimidoyloxy (—O—(C═NH)—CCl$_3$; see Example 4D), nitrate, alkyl phosphate, alkyl borate, trialkylammonium, and dialkylsulfonium. Preferred leaving groups are tosylate, mesylate, fluorosulfonate, trifluoromethylsulfonate, nitrate, and alkyl phosphates or boronates, represented by —OP(O)(OR)$_2$, and —OB(OR)$_2$, where R is hydrogen or lower alkyl.

Figure 5:
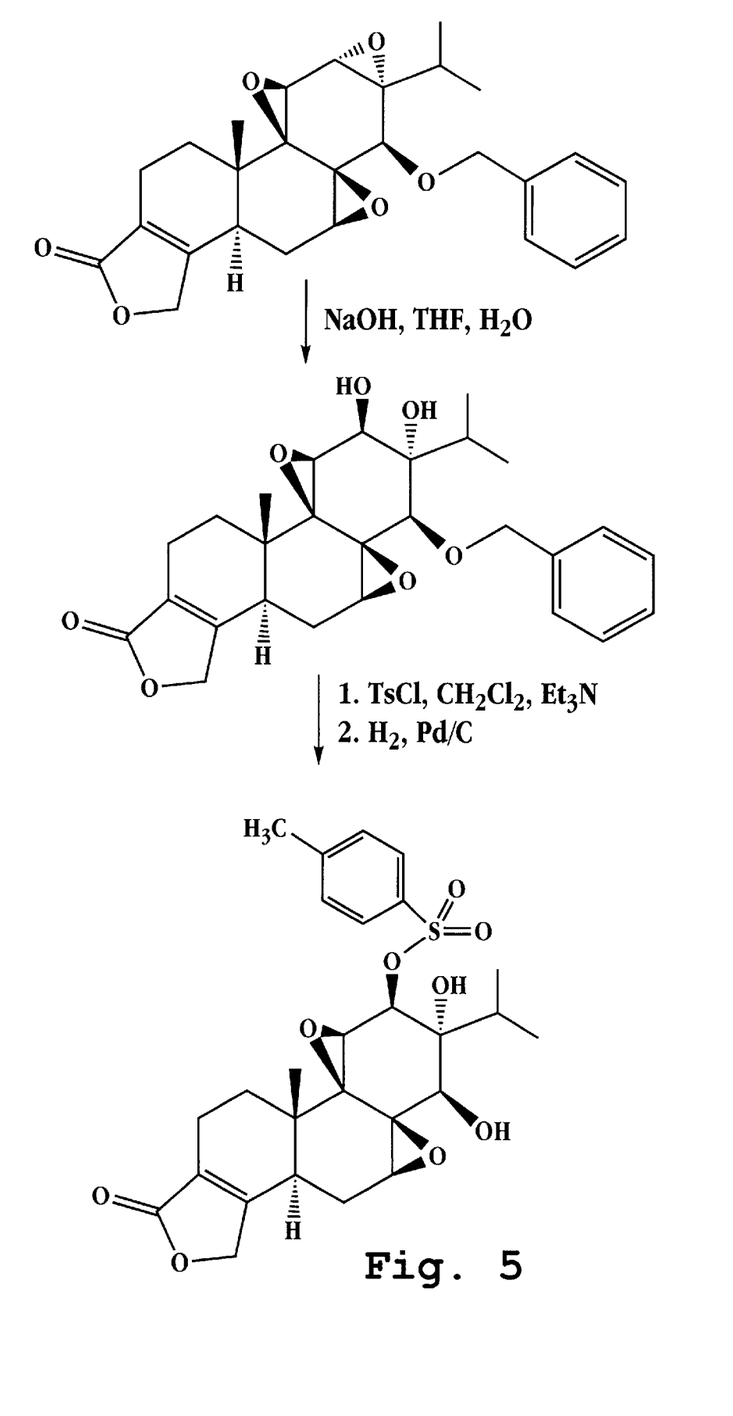
FIG. 5 shows the preparation of an epoxy ring-opened derivative of triptolide, in accordance with structure III.

These compounds are prepared by base-catalyzed ring opening of the 12,13 epoxy group of triptolide, as illustrated in FIG. 5 and described in Example 4A. As noted in Yu et al., the 12,13 epoxide of triptolide is less sterically hindered and reacts more readily than the 7,8 and 9,11 epoxides. The epoxide is regenerated in vivo by displacement of the 12-leaving group, restoring the triptolide structure.

Figures 6A, 6B:
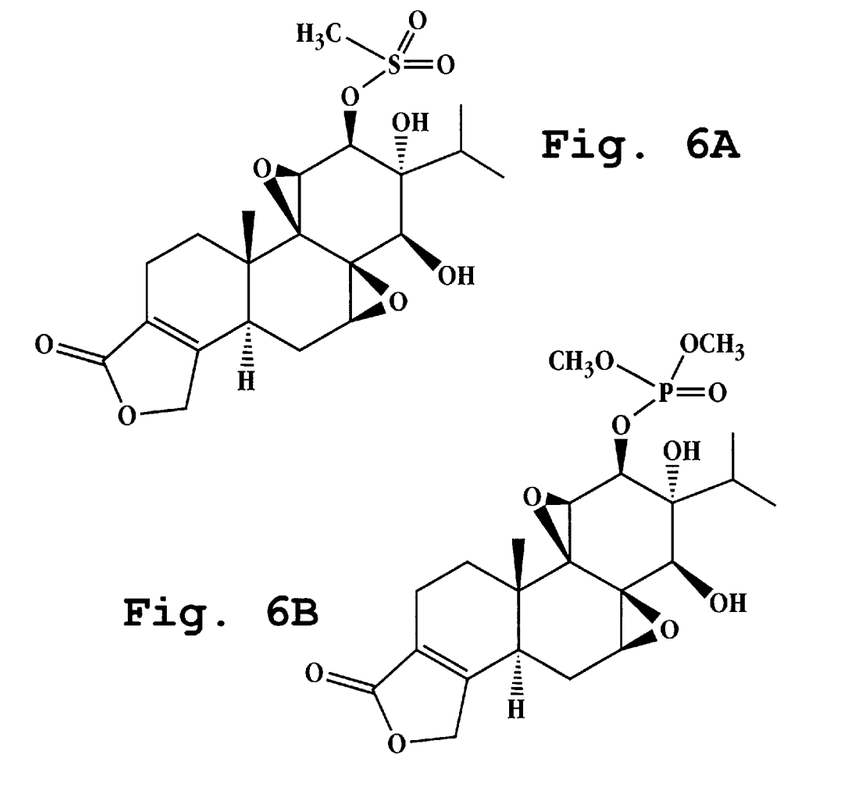
FIGS. 6A–6C show examples of specific embodiments of structure III.
Figure 6C:
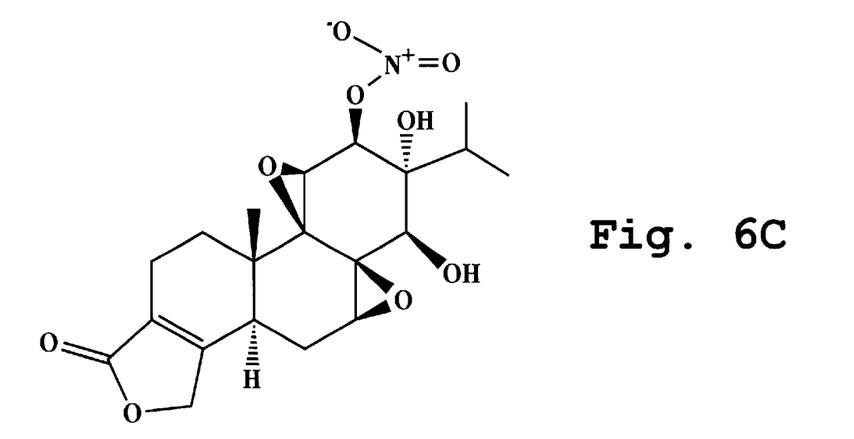

In the synthesis shown in FIG. 5, the hydroxyl at C14 is first protected as a benzyl ether, which is later removed by hydrogenation. The nucleophile, typically hydroxide ion, attacks at the less hindered 12-carbon of the epoxide. The resulting 12-hydroxyl group of the 1,2-diol is then converted to the leaving group $R^6$, in this case a tosylate. Other examples of compounds of structure III are shown in FIGS. 6A–6C. The synthesis of the 12-trifluoroacetate, trichloroacetate, trichloroacetimidoyloxy derivatives is described in Examples 4B–D.

If desired, the 13-hydroxyl (and 14-hydroxyl) may be converted to a hydrolyzable group, so that the compound will be more stable upon storage, but will still convert (albeit more slowly) to the epoxide in vivo. Because the 13-hydroxyl is tertiary and thus slow to react, use of an unhindered, reactive acylating agent, e.g., acetyl chloride, is preferred.

III. Therapeutic Compositions

Formulations containing the triptolide analogs of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide analog in a suitable intravenous solution, such as sterile physiological salt solution.

Liquid compositions can be prepared by dissolving or dispersing the triptolide analog (about 0.5% to about 20%) and optional pharmaceutical adjuvants in a pharmaceutically acceptable carrier, such as, for example, aqueous saline, aqueous dextrose, glycerol, or ethanol, to form a solution or suspension. The high water solubility of the compounds of the invention make them particularly advantageous for administering in aqueous solution, e.g. by intraperitoneal injection. Although aqueous solutions are preferred, compositions in accordance with the invention may also be formulated as a suspension in a lipid (e.g., a triglyceride, a phospholipid, or a polyethoxylated castor oil such as "CREMOPHOR EL™"), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in a pharmaceutically effective amount for effecting immunosuppression in a subject.

IV. Immunomodulating and Antiinflammatory Treatment

The compositions of the present invention are useful in applications for which triptolide has proven effective, e.g. in immunosuppression therapy, as in treating an autoimmune disease, preventing transplantation rejection, or treating or preventing graft-versus-host disease (GVHD). Triptolide and the present analogs are also useful for treatment of other inflammatory conditions, such as traumatic inflammation, and in reducing male fertility.

The method is useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The method is also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

In another aspect, the invention includes a method of treatment or prevention of graft-versus-host disease, resulting from transplantation into a recipient of matched or mismatched bone marrow, spleen cells, fetal tissue, cord blood, or mobilized or otherwise harvested stem cells. The dose is preferably in the range 0.25–2 mg/kg body weight/day, preferably 0.5–1 mg/kg/day, given orally or parenterally.

Also included are methods of treatment of autoimmune diseases or diseases having autoimmune manifestations, such as Addison's disease, autoimmune hemolytic anemia, autoimmune thyroiditis, Crohn's disease, diabetes (Type 1), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, and various allergies. In treating an autoimmune condition, the patient is given the composition on a periodic basis, e.g., 1–2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1–25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

The compounds are also useful as potentiators when administered concurrently with another immunosuppressive drug for immunosuppressive treatments as discussed above. A conventional immunosuppressant drug, such as cyclosporin A, FK506, azathioprine, rapamycin, mycophenolic acid, or a glucocorticoid, may thus be administered in an amount substantially less (e.g. 20% to 50% of the standard dose) than when the compound is administered alone. Alternatively, the triptolide analog and immunosuppresive drug are administered in amounts such that the resultant immunosuppression is greater than what would be expected or obtained from the sum of the effects obtained with the drug and triptolide analog used alone. Typically, the immunosuppressive drug and potentiator are administered at regular intervals over a time period of at least 2 weeks.

The compositions and method of the invention are also useful for the treatment of inflammatory conditions such as asthma, both intrinsic and extrinsic manifestations. For treatment of asthma, the composition is preferably administered via inhalation, but any conventional route of administration may be useful. The composition and method may also be used for treatment of other inflammatory conditions, including traumatic inflammation, inflammation in Lyme disease, psoriasis, chronic bronchitis (chronic infective lung disease), chronic sinusitis, sepsis associated acute respiratory distress syndrome, Behcet's disease, pulmonary sarcoidosis, pemphigus, pemphigoid inflammatory bowel disease, and ulcerative colitis.

The compositions of the invention may also be administered in combination with a conventional anti-inflammatory drug (or drugs), where the drug or amount of drug administered is, by itself, ineffective to induce the appropriate suppression or inhibition of inflammation.

The dose that is administered is preferably in the range of 1–25 mg/kg patient body weight per day, with lower amounts being preferred for parenteral administration, and higher amounts being preferred for oral administration. Optimum dosages can be determined by routine experimentation according to methods known in the art.

V. Anticancer Treatment

Triptolide prodrugs have shown effectiveness in cancer treatment. See, for example, copending and coowned U.S. application Ser. No. 09/766,156, which describes high efficacy of a triptoide prodrug, in comparison to 5-FU and CPT-11 in studies with tumor xenografts of the HT-29 human colon cancer cell line. The invention thus includes the use of a composition as described above to treat cancers, including cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease. and non-Hodgkin's lymphomas), the hematopoietic system, and epithelium (such as skin and gastrointestinal tract), solid organs, the nervous system, and musculo-skeletal tissue. The triptolide prodrugs may be used for treatment of various cancer cell types, including, but not limited to, breast, colon, small cell lung, large cell lung, prostate, malignant melanoma, liver, kidney, pancreatic, esophogeal, stomach, ovarian, cervical or lymphoma tumors. Treatment of breast, colon, lung, and prostate tumors is particularly contemplated. Treatment of leukemias is also contemplated. The composition may be administered to a patient afflicted with cancer and/or leukemia by any conventional route of administration, as discussed above.

The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

EXAMPLES

The following examples are intended to illustrate but not in any way limit the invention.

Example 1

Synthesis of 18-Glutaryl Furanoid Triptolide Analog (FIG. 1A) and Tromethamine Salt (FIG. 2B)

Triptolide (1 eq.) in dry THF is added dropwise, under an inert atmosphere, to a stirred suspension of a slight excess of NaH in dry THF at −78° C. After approx. 0.5 hr, glutaric anhydride (1 eq. or slight excess) is added dropwise, and the stirred mixture is allowed to come to room temperature over approx. 1 hr. The mixture is concentrated, taken up in ether, washed with water and brine, dried over anhydrous $MgSO_4$ and concentrated. The residue is purified by chromatography on silica gel.

To a stirred solution of 1 eq. of the glutaryl ester in THF is added a slight excess of a methanolic solution of tromethamine. The solution is concentrated, and the salt is recovered and dried under vacuum.

Example 2

Synthesis of 18-(1-Morpholino) Furanoid Triptolide Analog (FIG. 1B)

A THF solution of triptolide is treated with 1.1 equivalent morpholine. The reaction is mornitored by TLC. Upon completion, the solvent is removed under reduced pressure, and the residue is taken up in ether. The ether solution is washed with dilute aqueous HCl and dried with anhydrous MgSO$_4$ and concentrated to give the ring-opened amide.

The primary alcohol formed is protected as the t-butyldimethylsilyl ether with TBDMSCl and imidazole. The secondary alcohol at C14 is treated with acetic anhydride and a catalytic amount of DMAP to afford the acetate after aqueous work-up and extraction with ether. Concentration gives the crude product which is further purified by chromatography.

The purified product is subjected to hydrogenation with Pd/C catalysis. The catalyst is removed by filtration and the solution is concentrated to give the saturated amide. The t-butyldimethylsilyl group is then removed with 1.1 equivalent TBAF in THF, followed by an aqueous workup as described above. The primary alcohol is then oxidized to the aldehyde under Swern conditions (oxalyl chloride and Et$_3$N in DMSO).

Acetic anhydride is added to a stirred solution of the aldehyde in dichloromethane. The reaction mixture is slowly treated with perchloric acid with cooling. After the addition, the reaction mixture is further stirred for 24 h. The solvent is removed under reduced pressure to give the crude perchlorate salt. The crude salt is suspended in ether, and triethylamine is added dropwise with stirring. Upon completion of the reaction, the reaction mixture is diluted with ether and washed with water several times. The ether solution is dried over MgSO$_4$ and removed under reduced pressure. The crude aminofuran is purified by chromatography. If desired, the C14 acetyl group is removed by standard hydrolysis.

Example 3

Synthesis of Lactone Ring Opened Triptolide Analog (FIG. 3)

A solution of triptolide, excess (2-hydroxyethyl) morpholine and a catalytic amount of DMAP (dimethylaminopyridine) is stirred with mild heating in a polar aprotic solvent such as THF. The reaction is monitored by TLC. Upon completion, the reaction mixture is cooled, and acetic anhydride is added to acetylate the 14- and 19-hydroxyl groups. The solvent is removed under reduced pressure, and the residue is taken up in ether, washed several times with water and sodium bicarbonate solution, dried over anhydrous MgSO$_4$ and concentrated. If necessary, the product is purified by silica gel chromatography.

Example 4A

Synthesis of 12-tosyloxy-13-hydroxy triptolide (FIG. 5)

The 14-hydroxyl group is first protected by conversion to a benzyl ether. To avoid reaction of the acidic hydrogens of the conjugated lactone with basic reagents, such as metal hydrides, the compound (1 eq) is reacted with BzBr (2.5 eq) in the presence of Ag$_2$O (2 eq) in DMF under an inert atmosphere at 0° C. (see, for example, Mori et al.). The mixture is allowed to come to room temperature with stirring and stirred for about 24 h. The mixture is diluted with ether, washed with water and brine, dried over anhydrous MgSO$_4$ and concentrated. The residue is purified, if desired, by chromatography on silica gel.

The resulting 14-O-benzyl triptolide is then heated with NaOH in aqueous THF to convert the 12,13 epoxide to the diol. The solution is concentrated and the residue taken up in ether and worked up as above.

The diol (1 eq) is dissolved in CH$_2$Cl$_2$, and a solution of TsCl (1.5 eq) and triethylamine (1.5 eq) in the same solvent is added. After the reaction is complete by TLC, the mixture is washed with water and brine, dried over anhydrous MgSO$_4$, and concentrated. The residue is purified by silica gel chromatography.

The resulting benzyl ether-protected tosylate is dissolved in dry THF, 5% Pd/C (approx. 25 mg/meq of substrate) is added, and the mixture is purged with H$_2$ (atmospheric pressure) and stirred at room temperature until deprotection is complete, approx. 2–3 hrs. The solution is then filtered and concentrated to obtain the product.

Example 4B

Synthesis of 12-trifluoroacetoxy-13-hydroxy triptolide

14-O-Benzyl-12,13-dihydroxy triptolide (1 eq), prepared as described in Example 3A above, is dissolved in CH$_2$Cl$_2$, and triethylamine is added. To the solution is added trifluoroacetic anhydride (1.5 eq). After the reaction is complete by TLC, the mixture is washed with water and brine, dried over anhydrous MgSO$_4$, and concentrated. The residue is purified by silica gel chromatography. The resulting benzyl ether-protected trifluoroacetate is deprotected by catalytic hydrogenation as described above.

Example 4C

Synthesis of 12-trichloroacetoxy-13-hydroxy triptolide

The title compound is prepared by following the procedure in Example 3B, substituting trichloroacetic anhydride as acylating agent.

Example 4D

Synthesis of 12-trichloroacetimidoyloxy-13-hydroxy triptolide

14-O-Benzylated 12,13-dihydroxyl triptolide (1 eq), prepared as described in Example 3A, is reacted with NaOCH$_3$ (2.5 eq) in THF at room temperature for several hours. Trichloroacetonitrile (3 eq) is then added. After the reaction is complete by TLC, the mixture is concentrated. The residue is purified by recrystallization.

While the invention has been described with reference to specific methods and embodiments, it will be appreciated that various modifications may be made without departing from the invention.

What is claimed is:

1. A compound having the structure Ib:

where OR$^1$ is selected from
(i) a carboxylic ester, carbonate, or inorganic ester, having a central atom selected from carbon, sulfur, phosphorus, nitrogen, and boron, and having linked to said central atom at least one oxygen atom and at least one group —Y—Z or —O—Y—Z, where Y is a branched or unbranched $C_1$–$C_6$ alkyl or alkenyl chain, and Z is hydrogen or a polar group selected from keto, aldehyde, carboxylate, carboxylic ester, hydroxy, alkoxy, polyether, thiol, alkylthio, amino, ammonium, alkylamino, alkylammonium, cyano, nitro, sulfate, nitrate, phosphate, or a 5- to 7-membered heterocycle having ring atoms selected from carbon, nitrogen, oxygen, and sulfur, and three to six carbon ring atoms, and (ii) a mono-, di- or trisaccharide linked to C14 at an anomeric center;

and $OR^3$ is OH or O—(C=O)R, where R is lower alkyl.

2. The compound of claim 1, wherein $OR^1$ is selected from group (i).

3. The compound of claim 2, where $R^1$ is selected from (a)–(g) below:

where each R' is independently lower alkyl, R" is H or lower alkyl, n=1–4, m=1–2, and X=$CH_2$, O, or NR".

4. A compound having the structure Ic:

where $OR^3$ is OH or O—(C=O)R, where R is lower alkyl; and

$R^2$ is —(C=O)—Y—Z, where Y represents a branched or unbranched $C_1$–$C_6$ alkyl or alkenyl chain, and Z represents hydrogen, or, preferably, a polar group selected from keto, aldehyde, carboxylate, carboxylic ester, hydroxy, alkoxy, polyether, thiol, alkylthio, amino, ammonium, alkylamino, alkylammonium, cyano, nitro, sulfate, nitrate, phosphate, or a 5- to 7-membered heterocyclic ring whose ring atoms are selected from the group consisting of carbon, nitrogen, oxygen and sulfur, where the ring atoms include 3 to 6 carbon atoms.

5. The compound of claim 4, where $R^2$ is selected from (a)–(g) below:

-continued (g)

where each R' is independently lower alkyl, R" is H or lower alkyl, m=1–2, n=1–4, and X=CH$_2$, O, or NR".

6. A compound having the structure Id:

where

OR$^3$ is OH or O—(C=O)R, where R is lower alkyl, and each group R$^4$ is independently lower alkyl or together said groups form a 5- to 7-membered heterocycle having ring atoms selected from carbon, nitrogen, oxygen, and sulfur, and three to six carbon ring atoms;

or a pharmaceutically acceptable salt thereof.

7. A compound having the stricture II:

II where R$^5$ is selected from (a)–(d) below:

(a)

(b)

(c)

-continued (d)

where each R' is independently lower alkyl, n=1–4, and X=CH$_2$, O, or NR", where R" is H or lower alkyl; and and OR$^3$ is —O—(C=O)R, where R is lower alkyl.

8. A compound having the structure III:

III where

R$^6$ is a leaving group selected from the group consisting of trifluoroacetate, trichloroacetate, and trichloroacetimidoyloxy.

9. A compound having the structure Ia:

Ia where

R$^1$ is selected from (a)–(d) below:

(a)

(b)

-continued

(c)

(d)

where
each R' is independently lower alkyl, n=1–4, and X=CH$_2$, O, or NR", where R" is H or lower alkyl; and
OR$^3$ is OH or O—(C=O)R, where R is lower alkyl.

10. A method of effecting immunosuppression, comprising administering to a subject in need of such treatment, in a pharmaceutically acceptable vehicle, an effective amount of a compound having the structure selected from the group consisting of Ia, Ib, Ic, Id, II, and III:

Ia

Ib

Ic

-continued

Id

II

III where
each of OR$^1$ and OR$^5$ is independently selected from
(i) a carboxylic ester, carbonate, or inorganic ester, having a central atom selected from carbon, sulfur, phosphorus, nitrogen, and boron, and having linked to said central atom at least one oxygen atom and at least one group —Y—Z or —O—Y—Z, where Y is a branched or unbranched C$_1$–C$_6$ alkyl or alkenyl chain, and Z is hydrogen or a polar group selected from keto, aldehyde, carboxylate, carboxylic ester, hydroxy, alkoxy, polyether, thiol, alkylthio, amino, ammonium, alkylamino, alkylammonium, cyano, nitro, sulfate, nitrate, phosphate, or a 5- to 7-membered heterocycle having ring atoms selected from carbon, nitrogen, oxygen, and sulfur, and three to six carbon ring atoms, and
(ii) a mono-, di- or trisaccharide linked to C14 at an anomeric center;
R$^2$ is —(C=O)—Y—Z, where Y represents a branched or unbranched C$_1$–C$_6$ alkyl or alkenyl chain, and Z represents hydrogen, or, preferably, a polar group selected from keto, aldehyde, carboxylate, carboxylic ester, hydroxy, alkoxy, polyether, thiol, alkylthio, amino, ammonium, alkylamino, alkylammonium, cyano, nitro, sulfate, nitrate, phosphate, or a 5- to 7-membered heterocyclic ring whose ring atoms are selected from the group consisting of carbon, nitrogen, oxygen and sulfur, where the ring atoms include 3 to 6 carbon atoms;

$R^3$ is H or —(C=O)R, where R is lower alkyl;

each group $R^4$ is independently lower alkyl or together said groups form a 5- to 7-membered heterocycle having ring atoms selected from carbon, nitrogen, oxygen, and sulfur, and three to six carbon ring atoms; and $R^6$ is a leaving group selected from the group consisting of alkyl sulfonate, fluoroalkyl sulfonate, aryl sulfonate, fluorosulfonate, trifluoroacetate, trichloroacetate, trichloroacetimidoyloxy, nitrate, alkyl phosphate, alkyl borate, trialkylammonium, and dialkylsulfonium.

11. The method of claim 10, wherein said immunosuppression comprises inhibition of transplant rejection.

12. The method of claim 10, wherein said immunosuppression comprises inhibition of graft-versus-host disease.

13. The method of claim 10, wherein said immunosuppression comprises treatment of an autoimmune disease.

* * * * *